(12) United States Patent
Liu et al.

(10) Patent No.: US 9,579,627 B2
(45) Date of Patent: Feb. 28, 2017

(54) CARBON MOLECULAR SIEVE AND PELLET COMPOSITIONS USEFUL FOR C2-C3 ALKANE/ALKENE SEPARATIONS

(71) Applicant: Dow Global Technologies LLC, Midland, MI (US)

(72) Inventors: Junqiang Liu, Midland, MI (US); Mark K. Brayden, Baton Rouge, LA (US); Edward M. Calverley, Midland, MI (US); Steven R. Lakso, Sanford, MI (US); Yujun Liu, Pearland, TX (US); Marcos V. Martinez, Rosharon, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/763,855

(22) PCT Filed: Mar. 24, 2014

(86) PCT No.: PCT/US2014/031537
§ 371 (c)(1),
(2) Date: Jul. 28, 2015

(87) PCT Pub. No.: WO2014/160624
PCT Pub. Date: Oct. 2, 2014

(65) Prior Publication Data
US 2016/0008787 A1   Jan. 14, 2016

Related U.S. Application Data

(60) Provisional application No. 61/805,656, filed on Mar. 27, 2013.

(51) Int. Cl.
| | | |
|---|---|---|
| C01B 31/02 | (2006.01) | |
| B01J 20/20 | (2006.01) | |
| C01B 31/08 | (2006.01) | |
| B01J 20/28 | (2006.01) | |
| B01J 20/30 | (2006.01) | |
| C01B 31/00 | (2006.01) | |
| C07C 7/12 | (2006.01) | |
| B01D 53/04 | (2006.01) | |
| B01D 53/047 | (2006.01) | |

(52) U.S. Cl.
CPC ......... B01J 20/20 (2013.01); B01J 20/28042 (2013.01); B01J 20/28078 (2013.01); B01J 20/28085 (2013.01); B01J 20/28092 (2013.01); B01J 20/3007 (2013.01); B01J 20/3028 (2013.01); B01J 20/3042 (2013.01); B01J 20/3078 (2013.01); C01B 31/00 (2013.01); C01B 31/02 (2013.01); C01B 31/08 (2013.01); C07C 7/12 (2013.01); B01D 53/047 (2013.01); B01D 53/0462 (2013.01); B01D 2253/102 (2013.01); B01D 2253/116 (2013.01); B01D 2253/304 (2013.01); B01D 2257/7022 (2013.01); C01P 2004/54 (2013.01); C01P 2004/60 (2013.01); C01P 2006/16 (2013.01); C01P 2006/17 (2013.01)

(58) Field of Classification Search
CPC ....... C01B 31/02; C01B 31/08; C01P 2006/17
See application file for complete search history.

(56) References Cited

U.S. PATENT DOCUMENTS

| | | | |
|---|---|---|---|
| 4,070,446 | A | 1/1978 | Horikiri et al. |
| 4,775,655 | A | 10/1988 | Edwards et al. |
| 5,094,754 | A | 3/1992 | Maroldo et al. |
| 6,562,110 | B2 | 5/2003 | Koros et al. |

FOREIGN PATENT DOCUMENTS

| | | |
|---|---|---|
| EP | 0119924 A2 | 9/1984 |
| EP | 0282053 A2 | 9/1988 |
| GB | 1525420 A | 9/1978 |
| WO | 2014/160624 A1 | 10/2014 |

OTHER PUBLICATIONS

Hayashi, J, Separation of Ethane/Ethylene and Propane/Propylene Systems with a Cargonized BPDA-pp'ODA Polyimide Membrane, Ind. Eng. Chem. Res. 1996, 35, 4176-4181.
Nakagawa, H, et al. "Control of micropore formation in the carbonized ion exchange resin by utilizing pillar effect," Carbon 37 1999 1455-1461.
Miura, K., Preparation of novel porous carbons supporting metal nanoparticles and their applications to energy and environmental related issues, J. Ind. Eng. Chem., vol. 11, No. 6, 2005, 797-817.
Amberlyst* 35WET product literature—large pore ion exchange resin Product Data Sheet.
PCT/US2014/031537, International Search Report & Written Opinion, mailed Aug. 6, 2014.
PCT/US2014/031537, International Preliminary Report on Patentability. Mailed Jun. 26, 2015.

*Primary Examiner* — Stuart Hendrickson
(74) *Attorney, Agent, or Firm* — Dinsmore & Shohl LLP (57) ABSTRACT

A novel microporous carbon molecular sieve may be used as the basis for carbon adsorbent pellets that have discrete areas of carbonized binder and of carbonized precursor, macropores having an average pore diameter greater than or equal to 1 micrometer and a total macroporosity of at least 30 percent, both as measured by mercury porosimetry, and micropores that are capable of selectively admitting a C2-C3 alkene and excluding a C2-C3 alkane, and a total microporosity ranging from 10 percent to 30 percent. The pellets may be prepared by pyrolyzing a pellet structure comprising a carbon forming, non-melting binder and a non-porous gel type sulfonated polystyrene precursor at a temperature ranging from 500° C. to 1000° C., under an inert atmosphere and other conditions suitable to form the described pellets. The pellets are particularly useful in pressure swing and temperature swing adsorption processes to separate C2-C3 alkane/alkene mixtures.

5 Claims, 4 Drawing Sheets

CARBON MOLECULAR SIEVE AND PELLET COMPOSITIONS USEFUL FOR C2-C3 ALKANE/ALKENE SEPARATIONS

This patent application claims the benefit of U.S. provisional patent application Ser. No. 61/805,656, filed Mar. 27, 2013, which is incorporated herein by reference in its entirety.

This invention relates to the field of carbon molecular sieves. More particularly, it relates to novel carbon molecular sieve compositions that may be pelletized and used in processes to separate C2-C3 alkanes and alkenes.

Carbon molecular sieves (CMSs) have been recognized for some time as offering uses as adsorbents, catalysts, catalyst supports, electrodes for batteries and fuel cells, and the like. The range of applications is, to a great extent, attributable to the properties of the carbon itself, which include generally high resistance to heat, acids, and alkalis; hydrophobicity; and high electrical conductance. Pore structure control is critical to effectiveness of a molecular sieve in separations processes, because it is what determines selectivity.

Researchers in the field have attempted to prepare CMSs beginning with a variety of carbonaceous materials. Two publications, including Miura, K., "Preparation of novel porous carbons supporting metal nanoparticles and their applications to energy and environment related issues," *J. Ind. Eng. Chem.*, Vol. 11, No. 6, (2005) 797-817, and Miura, K., et al. "Control of micropore formation in the carbonized ion exchange resin by utilizing pillar effect," *Carbon* 37 (1999) 1455-1461, discuss preparation of a CMS from 0.5 millimeter (500 micrometers) diameter polystyrene-based ion exchange resin beads having sulfonic acid groups as the ion exchangeable groups. These works recognize that the sulfonic acid groups provide a mechanism to form pores as a result of heat treatment.

In one aspect the invention provides a process to prepare a carbon adsorbent pellet composition comprising pyrolyzing a pellet structure comprising a carbon forming, non-melting binder and a non-porous gel type sulfonated polystyrene precursor under an inert atmosphere and at a temperature ranging from 750 degrees Celsius (° C.) to 1000° C., under conditions suitable to form a pellet structure having discrete areas of carbonized binder and of carbonized gel type sulfonated polystyrene precursor, and wherein the pellet structure comprises macropores having an average pore diameter of at least 1 micrometer and a total macroporosity of at least 30 percent (%), both as measured by mercury porosimetry, and micropores capable of admitting a C2-C3 alkene and excluding a C2-C3 alkane, and having a total microporosity ranging from 10% to 30%.

In another aspect the invention provides the carbon adsorbent pellet prepared from the described process.

In yet another aspect the invention provides a carbon adsorbent pellet composition comprising macropores having an average pore diameter of at least 1 micrometer and a total macroporosity of at least 30%, both as measured by mercury porosimetry, and micropores capable of admitting a C2-C3 alkene and excluding a C2-C3 alkane, and having a total microporosity ranging from 10% to 30%.

In still another aspect the invention provides a pressure swing or temperature swing adsorption process comprising feeding a gas, comprising a C2-C3 alkane and a C2-C3 alkene, through a separation bed that includes the carbon adsorbent pellet described hereinabove; the process being carried out under pressure swing or temperature swing adsorption conditions such that the C2-C3 alkane and the C2-C3 alkene are substantially separated from each other.

In general the invention provides a combination of a particular CMS which can be pelletized and, especially in carbon adsorbent pellet form, then effectively used to separate C2-C3 alkanes from C2-C3 alkenes when such gases are present together in a mixture. The pellets' design includes molecular sieving micropores with significant C2-C3 alkane/alkene selectivity, which provides the actual gas separation, while the pellets also contain macropores that enable desirable levels of diffusivity through the pellets. Because of their pelletized structure, they also provide significant packing porosity, which further enhances gas stream diffusivity. The combination of these features allows for effective application of the pellets to a variety of processes, including but not limited to pressure swing and temperature swing adsorption processes.

To prepare the CMSs of the invention, a gel-type sulfonated polystyrene is selected as the starting material. Suitable polystyrenes may include any polystyrene based ion exchange resin having sulfonic acid groups as ion exchangeable groups. Such resin may also contain a proportion of a cross linking reagent, such as divinylbenzene, ranging from, desirably, 2 weight percent (wt %) to 16 wt %, based on weight of the ion exchange resin. In general a relatively higher degree of cross linking may be preferred, in some non-limiting embodiments, because the cross linking may reduce the level of pore shrinkage during the pyrolysis of the polystyrene. In particular embodiments the desirable ion exchange resin particle size may range from 1 micrometer (μm) to 100 μm, and more desirably from 1 μm to 50 μm.

Preparation of the desired starting non-porous gel-type sulfonated polystyrene may be by any means or method known to those skilled in the art. For example, where a cation exchanged resin is desired, cations such as $H^+$, $Ca^{2+}$, $Zn^{2+}$, $Cu^{2+}$, $Fe^{2+}$, $Ni^{2+}$, $Fe^{3+}$, and combinations thereof may be desirably selected. Exchange thereof may be carried out by, for example, embedding the raw resin in a column and treating with, for example, hydrogen chloride under suitable conditions, to first prepare the $H^4$ type resin. If a different cation is ultimately desired, the $H^+$ type resin may then be subsequently treated with an aqueous solution containing the desired cation, e.g., $Na^+$, $Ca^{2+}$, $Zn^{2+}$, $Cu^{2+}$, $Fe^{2+}$, $Ni^{2+}$, $Fe^{3+}$, or a combination thereof, to exchange the $H^+$ cation for the new cation. The effectiveness of cation exchange may be altered via control of the pH of the aqueous cation solution via addition of HCl.

Once the desired final gel-type sulfonated polystyrene is obtained, either via preparation as described hereinabove and/or via commercial purchase, it may in one embodiment be pyrolyzed, as is, to obtain a molecular sieve composition directly. In order to accomplish this pyrolysis, the gel-type sulfonated polystyrene precursor may be heated under conditions suitable to effect near or complete carbonization thereof. Preferably the carbon atomic content in the final CMS product is higher than 90% (measured by X-ray Photoelectron Spectroscopy), but a carbon atomic content ranging from 80% to 95% may be employed to ensure production of a desirable CMS. Pyrolysis may be carried out at a temperature ranging from 500° C. to 1000° C., preferably from 750° C. to 1000° C., more preferably from 800° C. to 900° C., and most preferably from 850° C. to 900° C. A time at final temperature ranging from 1 minute (min) to 240 min, preferably from 1 min to 30 min, and more preferably from 1 min to 10 min, may be employed. While those skilled in the art will be aware that a balance of time and temperature, in addition to alterations of other processing parameters, such as are known means of altering outcomes, may be employed, it has been found in the present invention that a temperature from 800° C. to 900° C., for a time ranging from 1 min to 30 min, at 1 standard atmosphere pressure (1 atm, approximately 101 kilopascals, kPa), and an inert nitrogen atmosphere, are particularly effective to ensure production of a preferred embodiment of the inventive CMS.

Such CMS is defined herein as having micropores that are capable of admitting an alkene selected from ethylene and propylene molecules, while excluding an alkane selected from ethane and propane molecules. This property may be easily determined by those skilled in the art via a simple test to determine whether separation of at least one of the C2-C3 alkene molecules, i.e., ethylene and/or propylene, is separated from at least one of the C2-C3 alkane molecules, i.e., ethane and/or propane, occurs when a mixture of the alkane and alkene molecules is passed across/through a bed of the CMSs. This separation implies an apparent micropore average pore diameter ranging from approximately 3.8 Angstroms (Å, 0.38 nanometers, nm) to 4.5 Å (0.45 nm), preferably from 3.9 Å (0.39 nm) to 4.2 Å (0.42 nm), and a total micoporosity ranging from 10% to 30%, preferably from 15% to 25%, and more preferably about 20%. The total microporosity is determined based on a skeletal density ranging from 1.0 grams per cubic centimeter ($g/cm^3$) to 2.0 $g/cm^3$.

While the CMSs are effective in separations, such have been found to be not always practical for use in typical commercial separation processes, simply because the CMSs, when prepared as described hereinabove, constitute finely divided powders. This morphology results in a very high pressure drop and relatively slow separation over the powder-containing packed bed due to diffusivity issues. Thus, the present invention has solved this problem by preferably using the CMSs as a basis for preparing useful pellets. This is done by first combining the gel-type sulfonated polystyrene precursor material (unpyrolyzed) with a carbon forming binder under suitable conditions to form a pellet precursor material.

The binder may be selected from any of a variety of non-melting, carbonaceous materials, i.e., materials that decompose to form carbon upon pyrolysis. By "non-melting" is meant that the binder does not have a melting temperature, i.e., a $T_g$. Such may include, but are not limited to, carbon itself, in forms such as but not limited to graphite, and carbon forming adhesives, such as cellulose ethers. Particularly preferred in some embodiments, for reasons of effectiveness, cost and convenience, are the methyl cellulose ethers.

In order to prepare the pelletizable precursor material it has been found useful, in one non-limiting embodiment, to first combine the starting gel-type sulfonated polystyrene particle with the binder. In preferred embodiments the binder is in an aqueous, 2 wt % solution and has a viscosity that is within a range of, for example, from 3000 centipoise (cP, 3 pascal seconds, Pa*s) to 5000 cP (5 Pa*s). The binder solution is combined with the gel type sulfonated polystyrene precursor material in an amount preferably from 2 wt % to 10 wt %, more preferably from 4 wt % to 6 wt %, based on weight of the gel type sulfonated polystyrene precursor material, and forms what may be roughly described as a paste having an apparent viscosity greater than 100,000 cP (100 Pa*s). This paste can be, in one particular embodiment, ram-extruded through a die to achieve a desired, unpyrolyzed pellet, also termed a raw pellet or pellet precursor, that has a preferred aspect ratio (length to width) ranging from 20:1 to 1:5, with overall greatest dimension, e.g., in some embodiments, length, preferably ranging from 1 millimeter (mm) to 10 mm, and more desirably from 1 mm to 5 mm. Those skilled in the art will understand that the shape, i.e., morphology, of the pellet can be varied and may include, in non-limiting example, cylindrical or spherical pellets, and that such morphology will affect, in well-known ways, the overall packing properties of the pellets in a separation bed. This will, in turn, affect the diffusivity and therefore the rate of separation attainable for a given bed.

In a final step, the raw pellets are pyrolyzed under suitable conditions such that the morphological characteristics of the raw pellets are maintained. This means that the pyrolyzed pellets, now termed carbon adsorbent pellets, still exhibit discrete, recognizable areas of binder and discrete, recognizable areas of sulfonated polystyrene precursor, albeit both are now essentially carbonized, with the areas of carbonized sulfonated polystyrene precursor (effectively now CMS areas) being preferably distributed in a relatively uniform fashion in (i.e., among the discrete areas of) the carbonized binder. In this relationship the carbonized binder areas serve to bind the CMS areas, but because the binder is in minor proportion, it does not form a true, continuous matrix, but rather simply and minimally serves to hold the higher proportion CMS areas together within the pellet structure. The resulting pyrolyzed carbon adsorbent pellets may thus be characterized as effectively having both the characteristic CMS micropores for molecular sieving and macropores for desirable gas diffusivity through the pellets, i.e., for desirable rates of gas transport. These macropores are defined as having an average pore diameter greater than or equal to 1 μm and a total macroporosity of at least 30%, both as measured by mercury porosimetry. In particular embodiments the total macroporosity is preferably at least 35%. Those skilled in the art will be able to conveniently determine these properties using conventional means and methods.

Furthermore, the carbon adsorbent pellets of the invention may, in particularly preferred embodiments, have sufficient structural integrity to ensure that the carbon adsorbent pellets, when aggregated in a separation bed, are not significantly crushed as a result of the weight of the packed bed. The carbon adsorbent pellets will desirably exhibit a crush strength of at least 0.10 pounds per millimeter (lbs/mm, approximately 0.045 kg/mm), preferably at least 1 lbs/mm (approximately 0.454 kg/mm), more preferably at least 2 lbs/mm (approximately 0.907 kg/mm), and most preferably at least 5 lbs/mm (approximately 2.268 kg/mm). In addition to desirable levels of crush strength, the carbon adsorbent pellets may exhibit a minimized increase in mass transfer resistance and minimized loss of adsorption kinetics when the pellets are compared with the (unpelletized) CMS compositions, i.e., the pelletization process does not, in certain particular embodiments, significantly interfere with the available separation-capable microporosity of the CMS particles included therein.

A particular application for the inventive pellets is use in separation beds for pressure swing adsorption processes. Such processes require adequate diffusivity between the pellets to enable industrially viable separation rates within acceptable pressure ranges. Those skilled in the art will understand that such inter-pellet porosity, resulting from the way the pellets are packed into the bed, affects mass transport as does the macroporosity of each pellet, and is therefore an additional diffusivity factor that should be taken into account in designing a pressure swing adsorption process. Such inter-pellet diffusivity, which may also be termed the "voids fraction" of the total aggregated pellets being employed, depends upon the geometry and aspect ratio of the pellets. For many applications, however, a voids fraction of at least 30% is desirable, and more desirable is a voids fraction of at least 35%.

As is well known in the art, a pressure swing adsorption separation may be generally carried out via the four basic steps of pressure swing adsorption: (1) pressurization, during which the mixture of gases to be separated, is fed to the separation bed; (2) adsorption, during which some defined gas included in the gas mixture is adsorbed by the separation medium, e.g., the pellets, within the bed; (3) blowdown, during which the separation bed is depressurized and the non-adsorbed gas is removed; and (4) desorption, during which an inert gas or portion of the purified gas is used to purge the adsorbent bed to desorb and remove the adsorbed gas from the bed.

Thus, in the case of, for example, a propylene/propane separation using the inventive carbon adsorbent pellets, in the adsorption stage the propylene would be absorbed into the inventive carbon adsorbent pellets from the propylene containing stream, and a purified/enriched propane stream (in preferred embodiments, more than 80% propane by volume, v/v) would be obtained. Then, during the desorption stage, the propylene would be desorbed from the carbon pellet adsorbent and collected as a purified/enriched propylene stream (in preferred embodiments, more than 80% propylene v/v) by purging with a small portion of the purified propane or an inert gas and/or by applying partial vacuum. A similar scenario can be applied for an ethylene/ethane separation.

It is noted that for industrial scale application a pressure swing adsorbent system might typically contain at least two columns packed with carbon adsorbent pellets to make a semi-continuous process. A fifth step, pressure equalization of the two separation columns, could then be added in order to further improve the separation performance.

In particular embodiments, conditions for a pressure swing adsorption process using the inventive carbon adsorbent pellets may preferably include a temperature ranging from 10° C. to 200° C., more preferably from 50° C. to 150° C.; an alkene partial pressure in the feed ranging from 0.1 bar (10 kilopascals, kPa) to 10 bar (1000 kPa), more preferably from 0.5 bar (50 kPa) to 3 bar (300 kPa); and an adsorption cycle time ranging from 1 min to 30 min, more preferably from 5 min to 15 min. Notwithstanding the above, those skilled in the art will be aware of a wide range of alterations in conditions of temperature, pressure, and adsorption cycle time that will be effective in carrying out an effective C2-C3 alkane/alkene separation.

Another application of the inventive pellets is use in separation beds for temperature swing adsorption processes. A temperature swing adsorption process generally includes using two adsorbent beds. While one bed undergoes the adsorption step, the other bed undergoes the regeneration step. The adsorption step occurs at a relatively lower temperature at which adsorption is favored over desorption. During this step a targeted gas that is included in the gas mixture is adsorbed and thereby separated from other gases in the mixture. The regeneration step includes both heating and cooling. During heating, a high temperature regeneration stream, normally an inert gas such as nitrogen, is introduced into and flows through the column that has just completed the adsorption step. The high temperature regeneration stream heats the adsorbent bed to a desired regeneration temperature and then maintains the bed at that temperature for a desired period of time. This results in the adsorbed gas desorbing from the adsorbent and leaving the column with the regeneration stream. To prepare the adsorbent bed for the adsorption step of the next cycle the adsorbent is then cooled by means of a stream, typically an inert gas, flowing through the adsorbent bed at a temperature close to the feed mixture temperature. Once the bed is cooled to the adsorption step temperature, it is ready for the next cycle.

For C2-C3 alkane/alkene separations, the temperature swing process's cycle time may desirably range from several to tens of hours, depending upon the scale. Temperature for adsorption may desirably range from ambient temperature to 90° C., preferably ambient to 60° C., and more preferably from ambient to 40° C. The regeneration temperature may preferably range from 150° C. to 250° C., preferably from 175° C. to 225° C.

In some non-limiting embodiments additional steps may be added to the temperature swing adsorption. In particular, temperature swing adsorption can be combined with pressure swing adsorption, i.e., adsorption is carried out at a higher pressure and low temperature, while desorption is carried out at a lower pressure and higher temperature, with purge. In this combined process, a blowdown step is typically added between the adsorption and regeneration steps, and a repressurization step is typically added between the regeneration and adsorption steps.

In particular embodiments of the pressure swing or temperature swing adsorption processes of the present invention, the C2-C3 alkane and C2-C3 alkene are substantially separated from each other. As the term is used herein, "substantially" means that at least 80% v/v, based on the total constituency of each gas in the starting mixed alkane/alkene feed, is separated from the other gas (or gases, if there are two of the named alkanes and/or two of the named alkenes in the feed) by the process. Preferably at least 85% v/v, and still more preferably at least 90% v/v, of each is separated. Furthermore, it is desirable that the alkene be at least 85% v/v of the final desorbed product, more desirably at least 90% v/v, and most desirably at least 95% v/v.

EXAMPLE 1

The DOWEX™ 50X8 (DOWEX is a trademark of The Dow Chemical Company) (U.S. mesh 200 to U.S. mesh 100; 74 μm to 149 μm) ion exchange resin is used as the gel type sulfonated polystyrene precursor. This precursor has 8 wt % of divinylbenzene cross linking reagent, based on weight of the resin.

The sulfonated polystyrene (3 grams, g) is pyrolyzed in a 1-inch (2.54 centimeters, cm) quartz tube furnace, purged with nitrogen at a flow rate 50 milliliters per minute (mL/min). The temperature is raised to 850° C. at a rate of 5° C./min. The temperature is then kept at 850° C. for 15 min. The tube furnace is left to cool down to room temperature and CMSs are collected.

The substantially uniform carbon beads exhibit, post-pyrolysis, an average size of about 80 μm, which is significantly smaller than the unpyrolyzed ion exchange resin beads of about 110 μm.

Figure 1:
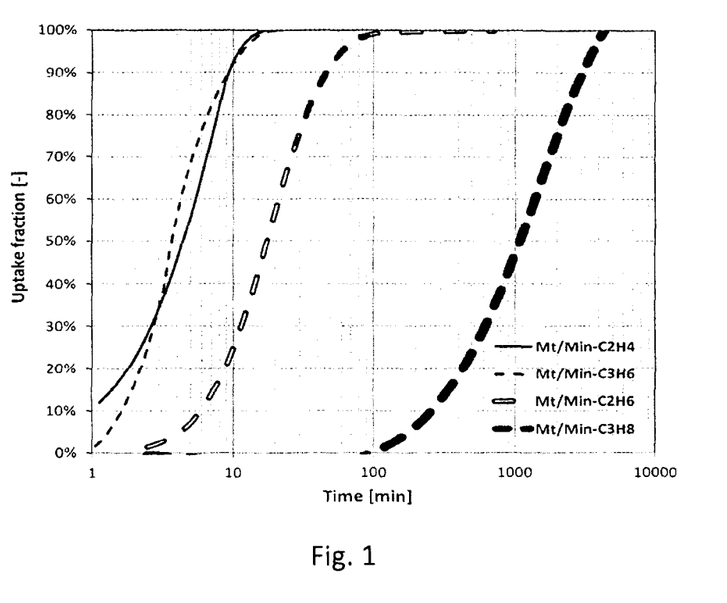
FIG. 1 shows the kinetic adsorption rate of ethylene, ethane, propylene, and propane gases into the CMSs in powder form.
Figure 2:
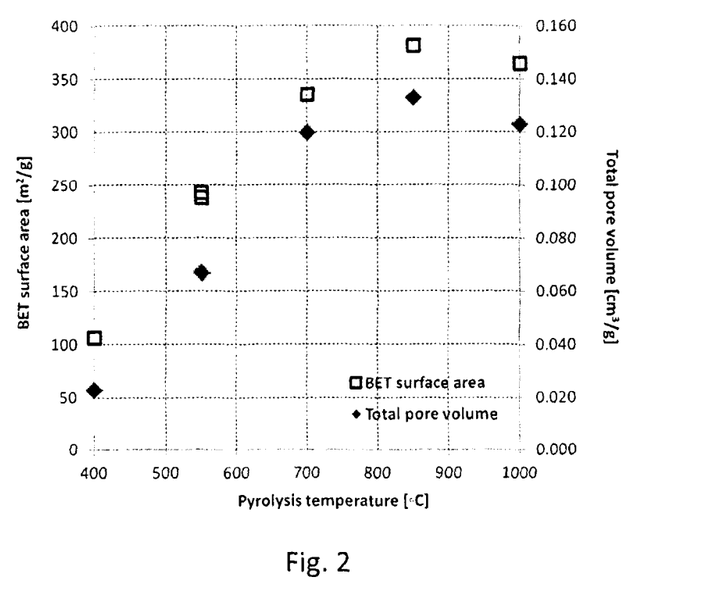
FIG. 2 shows the variation of micropore volume and surface area in the CMSs pyrolyzed over a temperature range.

The adsorption of four different gases (ethylene, ethane, propylene, propane) into the carbon molecular sieve beads is carried out at 10° C. It is known that the kinetic diameter of ethylene is 3.9 Å; ethane is 4.1 Å; propylene is 4.0 Å; and propane is 4.3 Å. See, for example, D. W. Breck, *Zeolite Molecular Sieves—Structure, Chemistry, and Use*, John Wiley & Sons, New York 1974. All four gases can diffuse into the inventive CMSs, but the diffusion rates are significantly different. The largest molecule, propane, diffuses into the CMSs significantly more slowly than the other three gases, and, in particular, than propylene, and this difference makes the CMSs prepared in this Example 1 particularly useful for separation of the two molecules. FIG. 2 shows the relative differences in adsorption speed among the four gases.

EXAMPLE 2

This example shows that average CMS micropore diameter can be altered by changing the pyrolysis conditions. As pyrolysis temperature increases, more micropores are generated, but at a certain degree of heat treatment, partial pore collapse, also termed "pore shrinkage," occurs.

The DOWEX™ 50X8 (U.S. 200 to 100 mesh size; 74 μm to 149 μm) ion exchange resin is used as the gel-type sulfonated polystyrene precursor. This precursor has 8 wt % of divinylbenzene cross linking reagent, based on weight of the resin. The sulfonated polystyrene (3 g) is pyrolyzed in a 1-inch (2.54 cm) quartz tube furnace, purged with nitrogen at a flow rate of 50 mL/min. The temperature is raised to a temperature from 550° C. to 1000° C. at a rate of 5° C./min. The maximum temperature is then maintained for 15 min. The tube furnace is left to cool down to room temperature and the CMSs are collected.

The total CMS micropore volume, measured in cubic centimeters per gram ($cm^3/g$), and surface area, measured by the Brunauer-Emmett-Teller method in cubic millimeters per gram ($mm^3/g$) by $CO_2$ adsorption, first increase up to a pyrolysis temperature of 850° C., then drop slightly at 1000° C. This is shown in FIG. 2.

Figure 3:
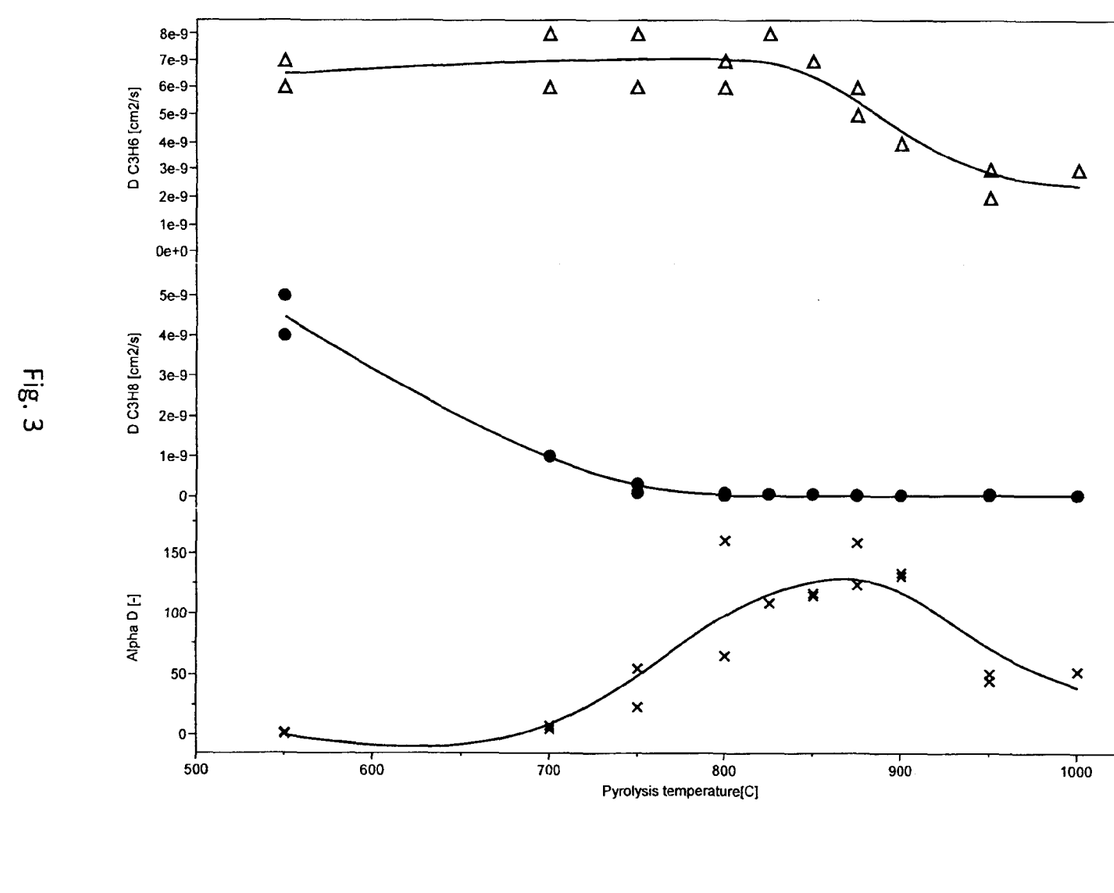
FIG. 3 shows the change of propylene and propane diffusivity, and propylene/propane diffusivity selectivity, for CMSs pyrolyzed from 550° C. to 1000° C.

FIG. 3 shows that the propylene diffusivity into the CMSs begins to drop after pyrolyzing at higher than 850° C., while the propane diffusivity starts to drop after pyrolyzing at a temperature higher than 700° C., and reaches a plateau at about 850° C. Thus, the propylene/propane diffusivity selectivity (measured as alpha-D) reaches its maximum of more than 100 when the pyrolysis has been carried out at a temperature ranging from approximately 850° C. to 900° C. for a time of 15 min.

EXAMPLE 3

An amount, 100 g, of dry ion exchange resin (DOWEX™ 50wX8, ranging in size from 400 U.S. mesh to 200 U.S. mesh, 37 μm to 74 μm), 100 g of deionized water and 4 g of METHOCEL™ A4M (a methyl cellulose ether available from The Dow Chemical Company) are mixed manually to make a viscous paste. The paste is extruded through a 3 mm die and automatically cut into approximately 2 mm in length, cylindrical carbon adsorbent pellets. The inventive pellets are dried in a nitrogen purged oven at 70° C. overnight. An amount, 10 g, of dried, raw pellets is pyrolyzed in a 1-inch (2.54 cm) tube furnace under a 50 mL/min flow of nitrogen. The furnace temperature is raised to a final temperature ranging from 550° C. to 1000° C. and held at the final temperature for 15 min, 30 min or 60 min. The furnace is left to cool down naturally and the carbon adsorbent pellets are collected. Table 1 shows the diffusivity (D) of propylene and of ethylene and also the propylene/propane and ethylene/ethane diffusivity selectivity (Alpha D) into the carbon adsorbent pellets pyrolyzed at a variety of final temperatures and hold times at such final temperatures, all prepared using a 5° C./min ramp rate.

TABLE 1

| Pyrolysis Temp. [° C.] (hold time) | D $C_3H_6$ [$cm^2/s$] | Alpha D $C_3H_6/C_3H_8$ | D $C_2H_4$ [$cm^2/s$] | Alpha D $C_2H_4/C_2H_6$ |
|---|---|---|---|---|
| 550 (15 min) | 5.9e-9 | 1.9 | 7.4e-9 | 1.1 |
| 600 (15 min) | 5.4e-9 | 1.8 | 7.8e-9 | 1.1 |
| 650 (15 min) | 5.1e-9 | 3.2 | 7.0e-9 | 1.1 |

TABLE 1-continued

| Pyrolysis Temp. [° C.] (hold time) | D $C_3H_6$ [cm²/s] | Alpha D $C_3H_6/C_3H_8$ | D $C_2H_4$ [cm²/s] | Alpha D $C_2H_4/C_2H_6$ |
|---|---|---|---|---|
| 700 (15 min) | 6.1e−9 | 8.2 | 7.7e−9 | 1.1 |
| 750 (15 min) | 6.3e−9 | 22.5 | 8.2e−9 | 1.3 |
| 800 (15 min) | 6.5e−9 | 76.3 | 8.7e−9 | 1.5 |
| 850 (15 min) | 5.4e−9 | 341.6 | 8.9e−9 | 3.6 |
| 900 (15 min) | 5.3e−9 | 132.1 | 6.6e−9 | 1.6 |
| 950 (15 min) | 1.7e−9 | 93.9 | 6.5e−9 | 22.9 |
| 1000 (15 min) | 1.4e−9 | 0.7 | 3.6e−9 | 26.9 |
| 1000 (30 min) | 5.6e−10 | 1.4 | 1.4e−9 | 46.7 |
| 1000 (60 min) | 1.0e−9 | 1.8 | 1.6e−9 | 16.7 |

EXAMPLE 4

An amount, 100 g, of dry ion exchange resin (DOWEX™ 50wX8, ranging in size from 400 U.S. mesh to 200 U.S. mesh, 37 μm to 74 μm), 100 g of deionized water and 5 g of METHOCEL™ A4M are mixed manually to make a viscous paste. The paste is extruded through a 3 mm die and automatically cut into approximately 2 mm in length, cylindrical pellets. The pellets are dried in a nitrogen purged oven at 70° C. overnight. An amount, 10 g, of dried, raw pellets is pyrolyzed in a 1-inch (2.54 cm) tube furnace under a 50 mL/min flow of nitrogen. The furnace temperature is raised to 850° C. at a ramp rate of 10° C./min, and then kept at 850° C. for 15 min. The furnace is left to cool down naturally and the carbon adsorbent pellets are collected. The carbon adsorbent pellets have macropores with an average pore diameter that is greater than or equal to 1 micrometer and a total macroporosity of at least 30 percent, both as measured by mercury porosimetry. They also have micropores that are capable of selectively admitting a C2-C3 alkene and excluding a C2-C3 alkane, and a total microporosity between 10 percent and 30 percent.

EXAMPLE 5

Two forms of adsorbent are used for pressure swing adsorption tests: CMS powder (i.e., not combined with binder prior to pyrolysis) and carbon adsorbent pellets (i.e., combined with binder, pelletized, and then pyrolyzed). The CMS powder is derived from a 400 U.S. mesh to 200 U.S. mesh (37 μm to 74 μm) gel-type, proton (H⁺) form, ion exchange resin identified as DOWEX™ 50wX8. The precursor is pyrolyzed at 825° C. for 15 min, with a temperature ramp rate of 5° C./min. The pellets are made by first pelletizing the resin, mixed with 5 weight percent (wt %) of METHOCEL™ A4M as binder, through an extruder with a 2.2 mm die and an automatic cutter to form raw pellets, followed by pyrolyzing the pellets in an inert atmosphere at 850° C. for 30 min, with a temperature rise rate of 6° C./min, to form carbon adsorbent pellets.

Figure 4:
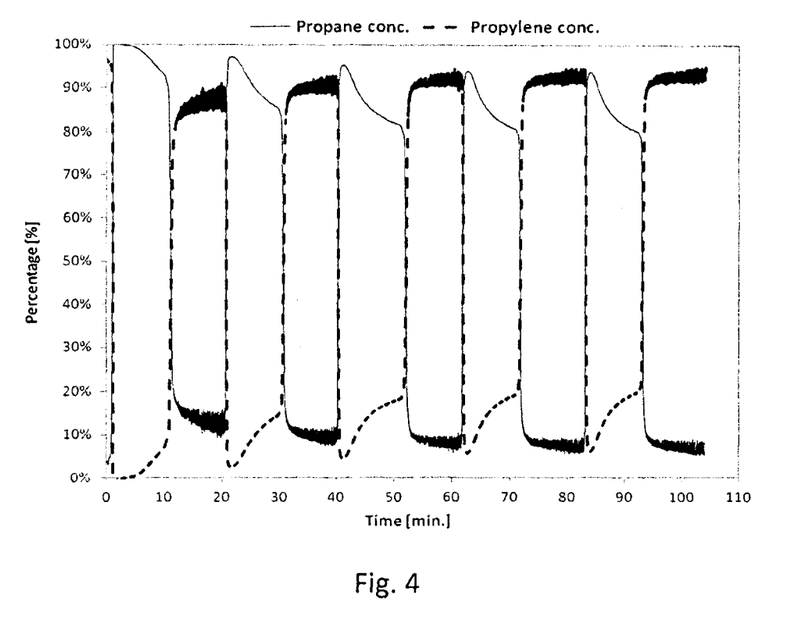
FIG. 4 shows the concentration of propylene and propane resulting from use of pellets over 10-minute adsorption/desorption cycles for Run #1.
Figure 5:
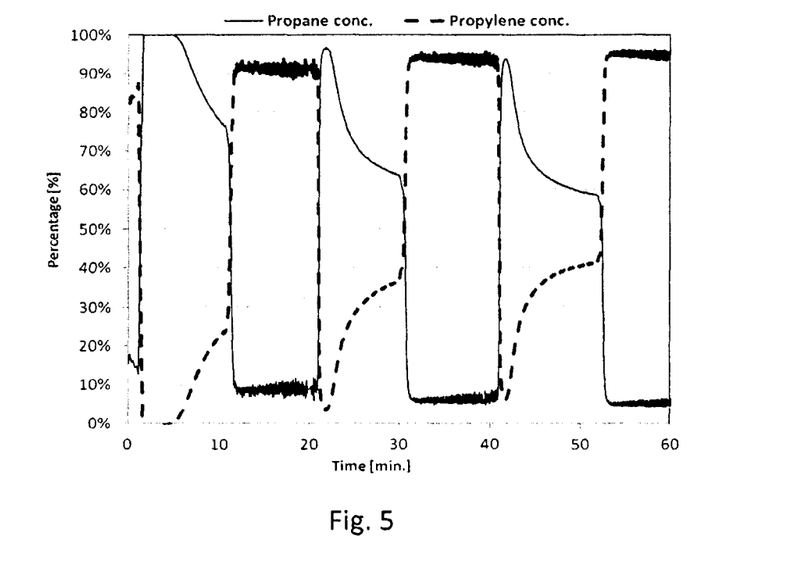
FIG. 5 shows the concentration of propylene and propane resulting from use of pellets over 10-minute adsorption/desorption cycles for Run #2.
Figure 6:
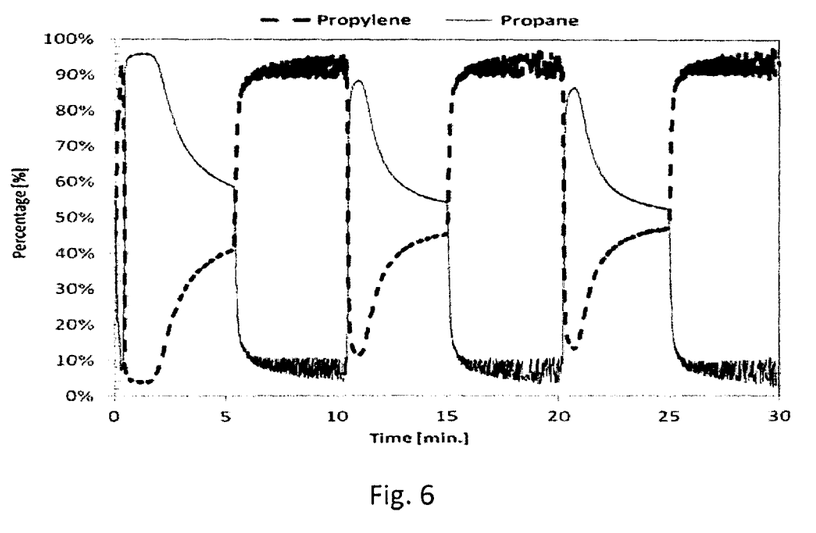
FIG. 6 shows the concentration of propylene and propane resulting from use of CMS powder over 5-minute adsorption/desorption cycles for Run #3.

The experimental details for preliminary pressure swing adsorption tests of the described carbon adsorbent pellets are shown in Table 2. The CMS (unpelletized) powder or carbon adsorbent pellets are packed into a 1-inch (2.54 cm) internal diameter stainless steel column. A propylene/propane mixture stream is introduced into the packed bed column at a constant flow rate for a standard amount of time (adsorption step time). The propylene and propane concentrations are monitored continuously. A nitrogen purge at a constant flow rate is then introduced during the desorption step for a standard amount of time (desorption step time), in order to reduce the partial pressure of propylene and propane in the bulk phase. (A partial vacuum could alternatively have been selected for the desorption step.) The propylene and propane concentration is monitored continuously. The adsorption/desorption is then switched for several cycles continuously. It is found that the powder exhibits a greater degree of pressure drop than do the pellets, which is expected because of the powder's inherently lower voids fraction in the column, but that the powder and pellets exhibit comparable gas selectivity, based on concentration as shown in FIGS. 4, 5, and 6, when the results are compared on a nitrogen-free basis.

TABLE 2

Parameters for swing adsorption tests.

| Run # | FIG. # | Adsorbent size and type | Adsorbent amount [g] | Temp. [° C.] | $C_3H_6$ ads. pressure [bar] | $C_3H_6$ conc. in feed [%] | Ads./Des. cycle time [min] | Feed flow rate | Des. $N_2$ purge rate [sccm] |
|---|---|---|---|---|---|---|---|---|---|
| 1 | 4 | 1.5 mm pellet | 54 | 20 | 0.25 | 25 | 10 | 100 | 100 |
| 2 | 5 | 1.5 mm pellet | 54 | 20 | 0.5 | 50 | 10 | 100 | 100 |
| 3 | 6 | 80 μm powder | 54 | 20 | 0.45 | 50 | 5 | 300 | 300 |

What is claimed is:

1. A process to prepare a carbon adsorbent pellet composition comprising
   combining a carbon forming, non-melting binder and a non-porous gel-type sulfonated polystyrene precursor to form a pelletizable paste;
   forming a raw pellet structure from the pelletizable paste; and
   pyrolyzing the raw pellet structure,
   under an inert atmosphere and at a temperature ranging from 750° C. to 1000° C., to form a carbon adsorbent pellet composition having discrete areas of carbonized binder and of carbonized precursor;
   wherein the carbon adsorbent pellet composition comprises
      macropores having an average pore diameter greater than or equal to 1 micrometer and a total macroporosity of at least 30 percent, both as measured by mercury porosimetry, and
      micropores that are capable of selectively admitting a C2-C3 alkene and excluding a C2-C3 alkane and have an average pore diameter ranging from 0.38 nanometers to 0.45 nanometers, and a total microporosity ranging from 10 percent to 30 percent.

2. The process of claim 1 wherein the carbon forming, non-melting binder is a cellulose ether.

3. The process of claim 1 wherein the non-porous gel type sulfonated polystyrene precursor is sulfonated polystyrene ion exchange resin particles, wherein the polystyrene contains from 2 weight percent to 16 weight percent of divinylbenzene cross linking reagent and the particles have an average diameter ranging from 1 micrometer to 100 micrometers.

4. The process of claim 1 wherein the pyrolysis temperature ranges from 800° C. to 900° C. and the conditions include a time ranging from 1 minute to 240 minutes.

5. The process of any of claim 1 wherein the pellets range in greatest dimension from 1 millimeter to 5 millimeters and have an aspect ratio ranging from 20:1 to 1:5.

\* \* \* \* \*